United States Patent [19]

Larkin

[11] Patent Number: 4,831,191

[45] Date of Patent: May 16, 1989

[54] CATALYTIC CONVERSION OF ALLYL FORMATE TO CARBOXYLIC ACIDS

[75] Inventor: John M. Larkin, Austin, Tex.

[73] Assignee: Texaco Inc., White Plains, N.Y.

[21] Appl. No.: 867,341

[22] Filed: May 23, 1986

Related U.S. Application Data

[63] Continuation-in-part of Ser. No. 685,932, Dec. 12, 1984, abandoned.

[51] Int. Cl.$^4$ .................... C07C 51/14; C07C 51/12; C07C 53/124; C07C 55/12
[52] U.S. Cl. .................................. 562/517; 562/590; 562/606
[58] Field of Search .................. 562/517, 606, 590; 260/413

[56] References Cited

FOREIGN PATENT DOCUMENTS 60695 9/1982 European Pat. Off. ............ 562/517
1072979 1/1960 Fed. Rep. of Germany ...... 562/517

*Primary Examiner*—Vivian Garner
*Attorney, Agent, or Firm*—Jack H. Park; Kenneth R. Priem; Carl G. Ries

[57] ABSTRACT

Allyl formate is substantially selectively converted to isobutyric acid, n-butyric acid and/or glutaric acid by bringing the alyl formate into contact with activated carbon in the presence of carbon monoxide, water and formic acid and a halide promoted group VIII soluble metal catalyst optionally in the presence of a solvent. Isobutyric and n-butyric acids are preferentially formed in the presence of relatively low concentrations of water and formic acid whereas glutaric acid is preferentially formed in the presence of relatively higher concentrations of water and formic acid.

12 Claims, No Drawings

CATALYTIC CONVERSION OF ALLYL FORMATE TO CARBOXYLIC ACIDS

RELATED APPLICATION

This application is a continuation-in-part of copending Larkin U.S. patent application Ser. No. 06/685,932 filed Dec. 12, 1984, now abandoned, and entitled "Conversion of Allyl Formate to Carboxylic Acids".

BACKGROUND OF THE INVENTION

1. Field of the Invention

This invention relates to a method for the production of carboxylic acids. More particularly, this invention relates to the conversion of allyl formate to carboxylic acids including isobutyric acid, n-butyric acid and/or glutaric acid. In particular, the present invention is directed to a process wherein allyl formate is brought into contact with activated carbon in the presence of carbon monoxide, a soluble compound of a group VIII catalyst, a halide promoter and at least a minor amount of water and formic acid whereby the allyl formate is converted with good yield and selectivities to the corresponding carboxylic acids. Isobutyric and n-butyric acids are preferentially formed when the concentration of water and formic acid are comparatively low. Glutaric acid is preferentially formed in the presence of comparatively higher concentrations of water and formic acid. The desired conversion is not obtained in the absence of formic acid. Isobutyric acid, which is a precursor for use in the manufacture of methacrylic acid is the predominant butyric acid isomer.

2. Prior Art

Illing et al. West German patent No. 1,072,979 discloses the isomerization of primary, secondary and tertiary monohydric or polyhydric saturated aliphatic, cycloaliphatic or aryliphatic esters of formic acid to the corresponding carboxylic acids in the presence of a halogen promoted carbonyl-forming metal of the 6th, 7th or 8th group of the Periodic Table in the presence of a support and, preferably, an activator. The activator may be a compound of bismuth, antimony or boron. The catalyst may be applied to a support such as charcoal, extruded silica, kieselguhr, zeolites, aluminum, pumice or bentonite. The reaction is preferably conducted in the presence of inert gas such as carbon monoxide, carbon dioxide or nitrogen.

Ray European patent application No. 0060695 published Sep. 22, 1982, is directed to the coproduction of formic acid in $C_2$ to $C_{10}$ monocarboxylic acids by the aqueous carbonylation of $C_1$ to $C_9$ alkyl formates. The carbonylation is conducted in the presence of a halogen promoted supported or unsupported Group VIII noble metal (e.g., rhodium).

Woodhouse U.S. Pat. No. 1,946,254 discloses the preparation of monocarboxylic acids by passing a vaporized aliphatic monohydroxy alcohol, carbon monoxide and a halogen over activated carbon.

Wakamatsu et al. in U.S. Pat. No. 3,798,267 discloses the preparation of formic acid by contacting methyl formate with activated carbon in the presence of a halide promoter and carbon monoxide.

Antoniades U.S. Pat. No. 4,194,056 also discloses a process for the preparation of formic acid from methyl formate. In accordance with the Antoniades process, the methyl formate is brought into contact with a soluble rhodium salt catalyst in the presence of carbon monoxide and a halogen promoter.

Isogai U.S. Pat. No. 3,839,426 is more broadly directed to the preparation of organic carboxylic acids from formic acid esters, such as vinyl formate (Example 36) by contacting the formic acid ester with a group VIII or group IIb catalyst in the presence of carbon monoxide.

French patent No. 2,030,118 discloses a process wherein carboxylic acids, especially formic acid, are produced from methanol by reacting methanol and carbon monoxide over a solid activated carbon bed at a temperature of from 200° to about 500° C. and a pressure of about 100 to about 3000 psi (7–210 $Kg/cm^2$) using a halogen promoter which is either dispersed on the carbon bed or incorporated as a component of the catalyst system.

Copending coassigned U.S. patent application Ser. No. 478,830 filed Mar. 25, 1983, now abandoned, in the name of John M. Larkin and entitled "A Process for Alkanol Carbonylation to Carboxylic Acids Using the Novel Combination of Catalyst and Carbon Bed Components" discloses a process wherein an alkanol together with a halide promoter and a low concentration of a soluble metal catalyst is passed over a carbon bed in the presence of carbon monoxide.

Copending coassigned U.S. patent application Ser. No. 478,829 filed Mar. 25, 1983, now abandoned, in the name of John M. Larkin and Roger G. Duranleau and entitled "A Process for Producing Carboxylic Acids by Carbonylation of Alkanols Over a Carbon Catalyst" discloses a process wherein an alkanol and a halide promoter are passed over a carbon bed contained in a nickel or cobalt alloy reactor in the presence of carbon monoxide.

SUMMARY OF THE INVENTION

It has been surprisingly discovered in accordance with the present invention that allyl formate can be converted to isobutyric acid, n-butyric acid and/or glutaric acid by bringing the allyl formate into contact with a bed of activated carbon in the presence of carbon monoxide, water and formic acid and a halide promoted group VIII soluble metal catalyst optionally in the presence of a solvent. Isobutyric and n-butyric acids are preferentially formed in the presence of relatively low concentrations of water and formic acid whereas glutaric acid is preferentially formed in the presence of relatively higher concentrations of water and formic acid.

DETAILED DESCRIPTION OF THE INVENTION

The starting materials for the present invention are allyl formate, carbon monoxide, activated carbon, a soluble compound of a group VIII metal, a halide promoter, water and formic acid. The catalysts that are suitable for use in the practice of the present invention are compounds of group VIII metals that are soluble in allyl formate. The soluble metal catalyst may be chosen from a wide variety of organic and inorganic compounds, complexes, etc. as will be shown and illustrated below. It is only necessary that the catalyst precursor actually employed contain group VIII metals in a soluble state.

Generally, the metal species used are selected from the group VIII transition metals. Effective metals include cobalt, ruthenium, iron, nickel, rhodium, palladium, osmium, iridium and platinum. The soluble group VIII metal catalyst may be added to the reaction mixture in the form of a carbonyl as in the case of, for example, triruthenium dodecacarbonyl, dicobalt octacarbonyl, iron pentacarbonyl, nickel tetracarbonyl, diiron nonacarbonyl, tetracobalt dodecacarbonyl, etc. Alternately, the group VIII metal may be added as the salt of a mineral acid as in the case of, for example, ruthenium trichloride, iron (II) iodide, iron (III) nitrate, cobalt (II) nitrate, cobalt (II) chloride, nickel (II) iodide, etc. or as the salt of a suitable organic carboxylic acid such as, for example, cobalt (II) acetate, cobalt (III) acetate, nickel (II) propionate, iron (II) naphthenate, etc. As additional examples, the metal may be added to the reaction mixture as a complex with a trisubstituted phosphorous compound or as a salt of an enolate. Representative examples include cobalt (III) 2,4-pentanedionate and dichlorotris(triphenylphosphine)ruthenium(II), etc.

Preferred group VIII soluble transition metal catalysts include carbonyls and halides. Among the particularly preferred are cobalt and nickel compounds such as dicobalt octacarbonyl, cobalt diiodide, nickel dichloride, etc.

Another effective method of adding small quantities of group VIII transition metals is to dissolve the group VIII metal in the reaction medium as for example by contacting the reactants and halide promoters with nickel or cobalt alloys. A particularly preferred method of introducing the soluble group VIII metal by this procedure is to use a reactor, pumps, or conduits constructed of nickel or cobalt alloys where the nickel or cobalt constitute from about 2% to about 98% of the metal content of the alloy. Commercial nickel stainless steel or Hastelloy alloys are especially preferred. Among these suitable alloys may be mentioned 316 Stainless Steel and Hastelloy C alloys.

The catalyst need not be present except as a minor constituent of the total reaction mixture. Thus, effective results are obtainable when the group VIII metal constitutes from about 10 to about 1000 parts per million of the total reaction mixture, such as about 50 to about 150 ppm.

The halide promoter, which may suitably be an alkyl halide, should be present in a larger concentration, such as a concentration of about 1 to about 20 mol percent, based on the allyl formate. The halide promoting component of the catalyst system may be introduced into the reaction zone in liquid form or gaseous form or dissolved in a suitable solvent or reactant. Satisfactory halide promoters include hydrogen halides such as hydrogen iodide and gaseous hydriodic acid, alkyl halides containing 1 to 12 carbon atoms such as methyl iodide, ethyl iodide, 1-iodopropane, 2-iodobutane, 1-iodobutane, methyl bromide, ethyl bromide, benzyl iodide; dihalomethanes such as diiodomethane and acyl halides such as acetyl iodide may also be used. Other examples include the quaternary ammonium and phosphonium halides, examples of which include tetramethyl ammonium iodide, tetrabutyl phosphonium iodide, etc. Alkali and alkaline earth halides, such as cesium iodide, may also be used.

The carbon monoxide will normally be fed to the reaction zone in the form of a gas and may be used alone or in conjunction with up to 90% by volume of one or more other gases. These other gases may include inert gases such as nitrogen, argon, neon, etc. Hydrogen may also be present, but a part of the carbon monoxide will tend to react with the hydrogen thus rendering that part ineffective for the purpose of the present invention.

The activated carbon bed over which the liquid feed stream is passed can be a fixed or fluidized bed and is prepared from a porous solid. The density range of the solid should be about 0.03–2.5 $cm^3/gm$. Preferred density range is 0.05–1.5 $cm^3/g$. A fixed carbon bed can be prepared from porous carbon by pyrolysis of amorphous carbon. Activated carbons of this type have surface areas of 200–2000 $m^2/g$. Carbons can be preformed of compacted granules, powders, or particles. Animal, vegetable or petroleum sources can be used.

The activated carbon bed can optionally be washed to remove metallic components which may be present from the organic sources used to prepare the carbon. If washed, the treatment consists of a HF solution or $HNO_3$ solution where the ratio is about 600 to about 1000 ml of $HNO_3$ per 500 g carbon and the $HNO_3$ concentration in water is from about 2%–30%. If HF is used, the concentration in water should be from about 10–55%. Washing time may be from 5 minutes to 24 hours. Further, the acid washed carbon can be washed with $H_2O$ to remove excess acid.

Suitable sources of activated carbon which can be used in the process of this invention include NORIT® RB-1 or SORBONORIT® B-3 activated carbon.

NORIT® and SORBONORIT® are registered trademarks of the American Norit Company. Another suitable activated carbon which may be used is CARBORUNDUM® GAC-616G. CARBORUNDUM® is a registered trademark of Kennecott Corporation. These activated carbons, prepared by the manufacturers according to procedures developed by them, are in the form of granules or pellets, and are described as generally having a surface area of 1000–1200 $m^2/g$. Methods of manufacturing activated carbon are listed in the book: *Activated Carbon, Manufacture and Regeneration* by A. Yehaskel, Noyes Data Corporation, Park Ridge, N.J., 1978.

The quantity of soluble transition metal catalyst employed in the instant invention is not critical and may vary over a wide range. Metal concentrations can range from less than 5 (e.g., 1) to greater than 1000 ppm, depending on the activity of the metal species. In general, my improved process is desirably conducted in the presence of a catalytically effective quantity of the active metal species, in conjunction with a halide promoter, and optionally in the presence of a solvent which gives the desired products in reasonable yields. The reaction proceeds when employing as little as about 0.0001 wt. %, and even lesser amounts of group VIII metal catalyst together with about 0.1–50 wt. % of a halide promoter, basis the total weight of the reaction mixture. The upper concentration is dictated by a variety of factors including catalyst cost, partial pressures of carbon monoxide, operating temperature, etc. A soluble group VIII metal catalyst concentration of from about 0.002 to about 0.02 wt. % metal in conjunction with an alkyl halide promoter concentration of from about 5 to about 15 mol percent based on the total mols of reaction mixture is generally desirable in the practice of this invention.

As indicated, water and formic acid should also be present in the fled mixture. Water may be present in an amount from about 0.2 to about 50 mol percent based on the allyl formate. When water is present in an amount within the range of about 0.2 to about 10%, the formation of butyric, n-butyric and isobutyric acid is promoted. At higher concentrations, the preferred reaction product tends to be glutaric acid.

Formic acid should be present within the range of about 0.1 to about 50 mol percent. Again, when the formic acid is present within a comparatively low range of about 0.1 to about 5%, the butyric acids will be preferentially formed. At the higher concentrations of formic acid, the formation of glutaric acid is promoted. The desired conversion is not obtained in the absence of formic acid.

The unsaturated carbon-carbon bond in allyl formate is converted to saturated bonds in butyric or glutaric acids. The source of hydrogen for effecting this transformation is not known, but is throught to arise from formic acid, water, or a combination of the two. Hence the total moles of water and formic acid should be at least equivalent to the moles of allyl formate used.

Although a solvent is not necessary for the reactions to occur, a solvent may be provided for instance to cause better solubility of promoters or to facilitate product separation. Suitable solvents include carboxylic acids such as acetic, propionic, butyric, and isobutyric acids, hydrocarbons such as cyclohexane, toluene, n-decane and the like, and ketones such as acetone, 2-butanone, or 4-methyl-2-pentanone. Other suitable solvents may include the alkyl chlorides such as chlorobenzene, chlorocyclohexane, 1-chlorohexane, etc. Preferred solvents are carboxylic acids such as propionic and butyric acids. An especially preferred solvent is one of the butyric acid isomers formed during practice of this invention so that a portion of the product can be recycled as solvent. When employing a solvent, it may be provided in concentrations of 5–80% and preferably in concentrations of 10–60% based on the weight of allyl formate.

A fluidized carbon bed or ebullient carbon bed is prepared by providing agitated contact of the activated carbon particles with the mixture of reactant liquids and gases as for example by suspending the carbon particles in the gas/liquid stream.

The reaction is also suitably conducted using a reactor, such as a jacketed reactor, containing a bed of activated carbon over which the other reactants are passed.

After passing through the reactor, the reactants may be separated into unreacted feed components and products by any suitable means such as vacuum distillation.

The temperature to be used in conducting the reaction of the present invention is a variable which is dependent upon other reaction parameters including pressure, the concentration and choice of the particular species of soluble group VIII metal catalysts, etc. In general, temperatures within the range of about 200° to about 400° C. such as a temperature within the range of about 240° to about 350° C., are employed with superatmospheric pressures of carbon monoxide. A narrower temperature range of 240°–350° C. is preferred.

Superatmospheric pressures of 100 psi or greater lead to substantial yields of carboxylic acids by the process of this invention. A preferred operating range is from 500 psi to 4000 psi, although pressures above 4000 psi also provide useful yields of desired formic acid.

In all these syntheses, the amount of carbon monoxide present in the reaction mixture should be from about 5% to about 50% on a mole basis of the amount of allyl formate present. Preferably about 0.1 to about 0.3 moles of carbon monoxide per mole of allyl formate are used.

Residence time is another variable which may be used in controlling the course of the reaction.

When the reaction is conducted batch-wise in an autoclave, reaction times may suitably be within the range of about 1 to about 24 hours. When the reaction is conducted continuously, by passing the reactants over a bed of activated carbon, the liquid hourly feed rate may suitably be within the range of about 0.02 to about 1.0 w/hr/w.

SPECIFIC EXAMPLES (1) Preparation of Allyl Formate (5633-18)

A mixture of 2001.5 g HCOOH, 924 g allyl alcohol, and 9.64 g $BF_3.Et_2O$ was allowed to stand for 90 hours. Analysis of this crude product (used for Example 2) was as follows: 13.5% $H_2O$, 32.7% HCOOH, 8.1% $CH_2=CH-CH_2OH$, 45.1% allyl formate.

A portion of the crude allyl formate was distilled at atmospheric pressure. Material distilling at 87°–88° C. (head temp) was used for Example 4. Analysis as follows: 7.4% $H_2O$, 0.5% HCOOH, 3.7% $CH_2=CH-CH_2OH$, 84.2% allyl formate, 1.0% unknown component.

(2) Reaction of Crude Allyl Formate Mixture with CO in the Presence of $NiI_2$, HI, and Activated Carbon A 300 ml stirred glass-lined autoclave was charged with the following: 25.905 g of crude allyl formate from Example 1, which contained 32.7% formic acid, 40 ml of propionic acid, 8 ml of 57% aqueous HI, 0.055 g of $NiI_2.6H_2O$, 10.0 g of finely pulverized Sorbonorit® B-3 activated carbon. This mixture was maintained in a CO atmosphere while the sealed autoclave was heated to 250° C. It was maintained at 250° C. for 5 hours. Pressure ranged from 1225 psig to 1350 psig. When cool, a gas sample was taken; analysis indicated 23.5% $H_2$, 26.2% $CO_2$, 0.2% $CH_4$, and several heavier components.

The liner contents were filtered. Gas chromatographic analysis of volatile components of the filtrate indicated 1.8% isobutyric acid, 0.8% n-butyric acid, 54.1% propionic acid, 41.8% $H_2O$, and several small unidentified components.

A 34.35 g portion of the filtrate was distilled until the final pot temperature reached 170° C.; no more overhead was present at this point. Wet solids (18.04 g) remained. Analysis of the solids indicated the presence of glutaric acid salts and some carboxylic acid (analysis was by infra-red). Presence of paramagnetic material precluded an analysis by nuclear magnetic resonance.

(3) Reaction of Allyl Formate with CO, Allyl Iodide, and $HRh(Ph_3P)_3CO$ in the Presence of Activated Carbon A 183 ml glass-lined rocking autoclave was charged with 7.50 g commercial (Eastman) allyl formate, which did not contain formic acid, 0.75 g allyl iodide, 7.50 g of 4-methyl-2-pentanone, 0.050 g of $HRhCO(Ph_3P)_3$, and 1.50 g of Sorbonorit B-3 pulverized activated carbon. It was pressured to 400 psig with CO and heated to 190° C.; the resultant pressure was 620 psig. Heating at 189°–192° C. was continued for 6 hours; final pressure was 700 psig.

Analysis of the liner contents indicated that allyl formate was largely unconverted. Butyric acids were present in no more than trace quantities.

(4) Continuous Reaction of Allyl Formate with CO in the Presence of Cobalt(III) Acetylacetonate and Diiodomethane over Activated Carbon A liquid feed was prepared consisting of 1041 g of distilled allyl formate (from Example 1, which contained 0.5% formic acid), 100 g of $CH_2I_2$, and 0.060 g of cobalt(III) acetylacetonate. It was pumped through a Grade 316 stainless steel conduit using a pump with stainless steel wetted parts to a 25 ml Hastelloy C tubular reactor containing Sorbonorit B-3 activated carbon. Carbon monoxide was simultaneously metered to the reactor at 2–6 l/hr while the temperature and pressure of the reactor were systematically varied. The liquid feed rate was maintained constant at 0.17 ml/min. Analytical results of reactor effluent collected under several different conditions are indicated below:

TABLE I

| °C. Temp | psig Pressure | glc, A % | | | | | |
|---|---|---|---|---|---|---|---|
| | | $H_2O$ | HCOOH | HOAc[1] | Iso-butyric Acid | n-butyric Acid | Allyl Formate |
| 240 | 1525 | 12.4 | 16.5 | 6* | 5.1 | 6.6 | 5* |
| 263 | 1500 | 5.3 | 16.3 | 9.0 | 12.6 | 10.2 | 0.5 |
| 281 | 1550 | 10.6 | 12.8 | 5.7 | 28.0 | 21.6 | 0.7 |
| 281 | 2025 | 10.0 | 14.6 | 6.0 | 33.5 | 24.5 | 0.8 |

[1]HOAc is derived from $CH_2I_2$
*Estimated values: measured sum of HOAc and allyl formate is 11%

The foregoing examples have been given by way of illustration only and are not intended as limitations on the scope of this invention, which is defined by the following appended claims.

What is claimed is:

1. A process which comprises charging allyl formate, carbon monoxide, water and formic acid to a reaction zone and there bringing them into contact with activated carbon in the presence of a Group VIII metal catalyst that is soluble in allyl formate and a halide promoter at an elevated temperature and pressure to thereby provide a reaction product comprising n-butyric acid, isobutyric acid and/or glutaric acid, said elevated temperature being in the range of about 200° to about 400° C. and said elevated pressure being in the range of about 100 psi to about 4,000 psi, said water being present in said reaction zone in an amount within the range of about 0.2 to about 50 mole percent, based on said allyl formate and said formic acid being present in said reaction zone in an amount within the range of about 0.1 to about 50 mol percent, based on said allyl formate.

2. A process as in claim 1, wherein the reactants are brought into contact with the activated carbon at a temperature within the range of about 240° to about 350° C. and a pressure within the range of about 1500 to about 2100 psig and wherein the halide promoter is an iodide promoter.

3. A method as in claim 2, wherein the soluble group VIII metal catalyst is a soluble nickel or cobalt or rhodium catalyst.

4. A method as in claim 3, wherein the catalyst is nickel iodide and wherein the promoter is hydrogen iodide.

5. A method as in claim 3, wherein the promoter is allyl iodide and the catalyst is HRh CO(Ph$_3$P)$_3$.

6. A method as in claim 3, wherein the promoter is diiodomethane and the catalyst is cobalt(III) acetylacetonate.

7. A process which comprises charging allyl formate, from about 5 to about 50 mole percent of carbon monoxide based on the allyl formate of allyl formate, from about 1 to about 20 mole percent, based on the allyl formate, of a halide promoter, from about 0.2 to about 50 mole percent, based on the allyl formate, of water, and from about 0.1 to about 50 mole percent, based on the allyl formate, of formic acid to a reaction zone and there bringing them into contact with activated carbon and from about 10 to about 1000 parts per million of the total reaction mixture of a soluble group VIII metal catalyst under reaction conditions including a temperature within the range of about 200° to about 400° C. and a pressure within the range of about 100 to about 4000 psi to thereby provide a reaction product comprising n-butyric acid, isobutyric acid and/or glutaric acid, said activated carbon being activated carbon having a density of from about 0.03 to about 2.5 cm$^3$/gm and a surface area of about 200 to about 2000 m$^2$ per gm.

8. A process as in claim 7, wherein the catalyst is present in an amount within the range of about 50 to about 150 parts per million, based on the total reaction mixture, the water is present within an amount within the range of about 0.2 to about 10 mole percent, based on the allyl formate, the formic acid is present in the range of from about 0.1 to about 5 mole percent, based on the allyl formate, the reaction temperature is within the range of about 240° to about 350° C., the reaction pressure is within the range of about 500 to about 4000 psi, and the carbon monoxide is present in the range of about 0.1 to about 0.3 moles of carbon monoxide per mole of allyl formate to thereby provide a reaction product comprising n-butyric acid and isobutyric acid.

9. A method as in claim 8, wherein the soluble group VIII metal catalyst is a soluble nickel or cobalt or rhodium catalyst.

10. A method as in claim 9, wherein the catalyst is nickel iodide and wherein the promoter is hydrogen iodide.

11. A method as in claim 9, wherein the promoter is allyl iodide and the catalyst is HRh CO(Ph$_3$P)$_3$.

12. A method as in claim 9, wherein the promoter is diiodomethane and the catalyst is cobalt(III) acetylacetonate.

* * * * *